(12) United States Patent
Wood et al.

(10) Patent No.: US 11,179,172 B2
(45) Date of Patent: Nov. 23, 2021

(54) TISSUE RESECTING INSTRUMENT

(71) Applicant: Covidien LP, Mansfield, MA (US)

(72) Inventors: Timothy J. Wood, Wilmington, MA (US); Dalia Leibowitz, Cambridge, MA (US); Peter Marshall, Bolton, MA (US)

(73) Assignee: Covidien LP, Mansfield, MA (US)

( * ) Notice: Subject to any disclaimer, the term of this patent is extended or adjusted under 35 U.S.C. 154(b) by 165 days.

(21) Appl. No.: 16/704,066

(22) Filed: Dec. 5, 2019

(65) Prior Publication Data
US 2021/0169512 A1    Jun. 10, 2021

(51) Int. Cl.
*A61B 17/32* (2006.01)
*A61B 34/37* (2016.01)
*A61B 17/00* (2006.01)

(52) U.S. Cl.
CPC ........ *A61B 17/32002* (2013.01); *A61B 34/37* (2016.02); *A61B 2017/0023* (2013.01); *A61B 2017/0046* (2013.01); *A61B 2017/00424* (2013.01); *A61B 2017/00477* (2013.01); *A61B 2017/00734* (2013.01); *A61B 2017/320028* (2013.01); *A61B 2217/005* (2013.01)

(58) Field of Classification Search
CPC ...... A61B 17/32002; A61B 17/320783; A61B 34/37; A61B 2017/0023; A61B 2017/00424; A61B 2017/0046; A61B 2017/00477; A61B 2017/00734; A61B 2017/320028; A61B 2017/00982; A61B 2017/320024; A61B 2217/005; B26B 25/002; A01D 34/412; A01D 34/42; A01D 34/56
See application file for complete search history.

(56) References Cited

U.S. PATENT DOCUMENTS

| | | | |
|---|---|---|---|
| 1,585,934 | A | 5/1926 | Muir |
| 1,666,332 | A | 4/1928 | Hirsch |
| 1,831,786 | A | 11/1931 | Duncan |
| 2,708,437 | A | 5/1955 | Hutchins |

(Continued)

FOREIGN PATENT DOCUMENTS

| | | | |
|---|---|---|---|
| DE | 3339322 A1 | 5/1984 | |
| DE | 3206381 C2 | 7/1986 | |

(Continued)

*Primary Examiner* — Erich G Herbermann
(74) *Attorney, Agent, or Firm* — Carter, DeLuca & Farrell LLP

(57) ABSTRACT

A tissue-resecting end effector includes an outer shaft having a hub housing, an inner shaft including a sun gear, and a drive assembly disposed within the hub housing. The drive assembly includes a first and second drivers disposed about the inner shaft distally and proximally of the sun gear, respectively. The drive assembly further includes a plurality of planetary gears radially disposed about and in meshed engagement with the sun gear between the drivers, and a locking clip proximal of the planetary gears and the sun gear, rotationally keyed to the second driver, and engaged with the first driver via at least one snap-fit engagement. The locking clip retains the drivers and the planetary gears in operable engagement with one another and the sun gear such that a rotational input provided to the second driver drives rotation of the inner shaft.

10 Claims, 12 Drawing Sheets

(56) References Cited

U.S. PATENT DOCUMENTS

| | | |
|---|---|---|
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |

(56) References Cited

U.S. PATENT DOCUMENTS

| | | |
|---|---|---|
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2013/0131452 A1 | 5/2013 | Kuroda et al. |
| 2014/0003183 A1 | 1/2014 | Song |
| 2018/0028212 A1* | 2/2018 | Akilian .......... A61B 17/320783 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |

(56) References Cited

FOREIGN PATENT DOCUMENTS

| | | |
|---|---|---|
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

* cited by examiner

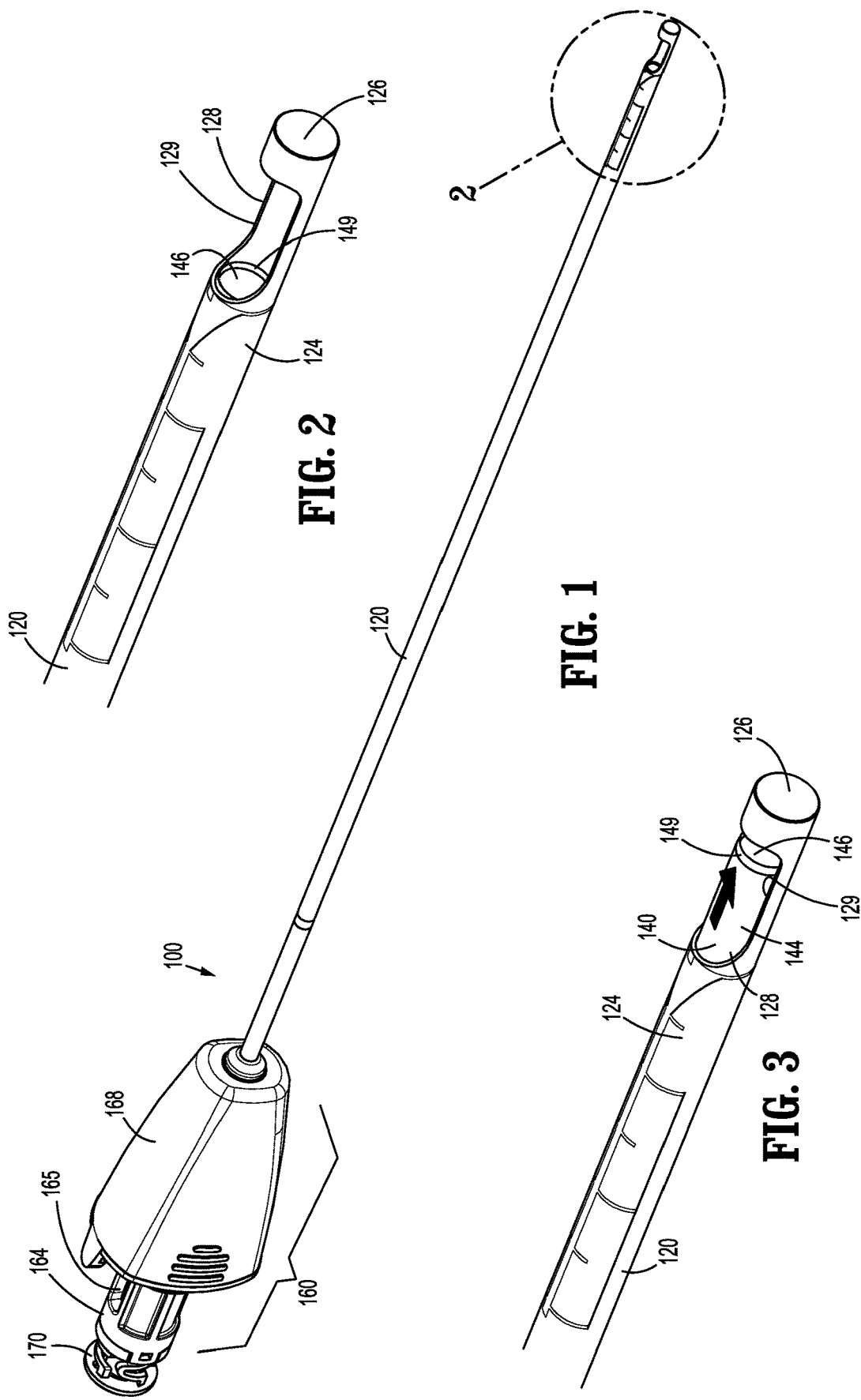

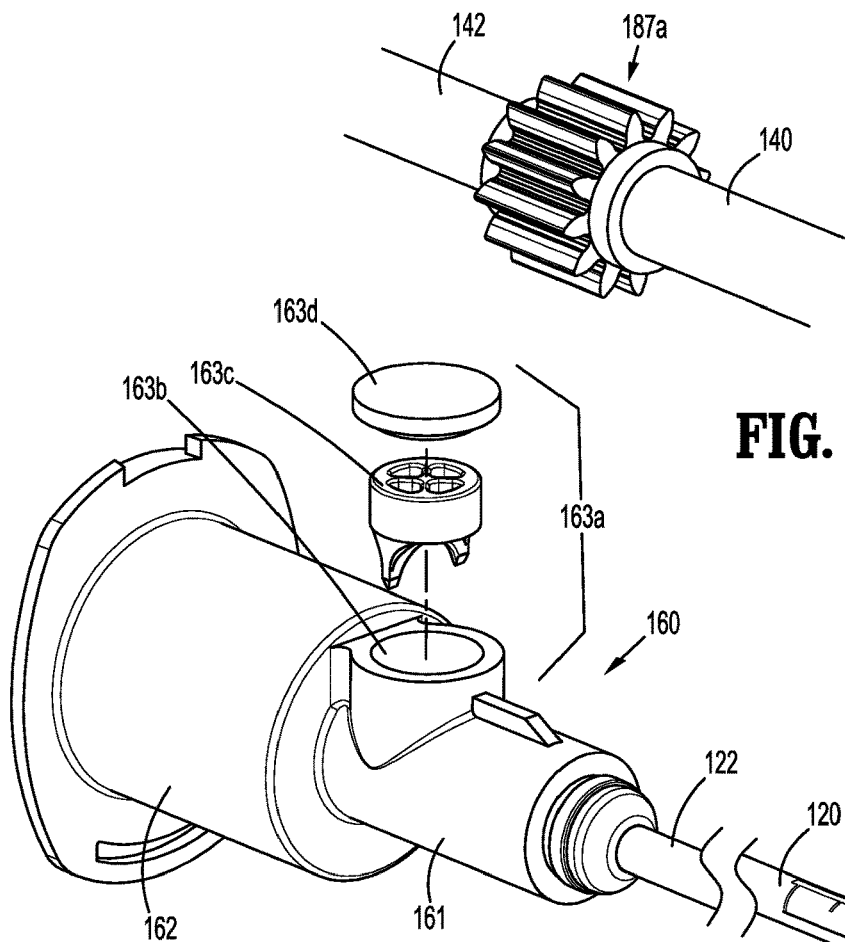
FIG. 5
FIG. 6
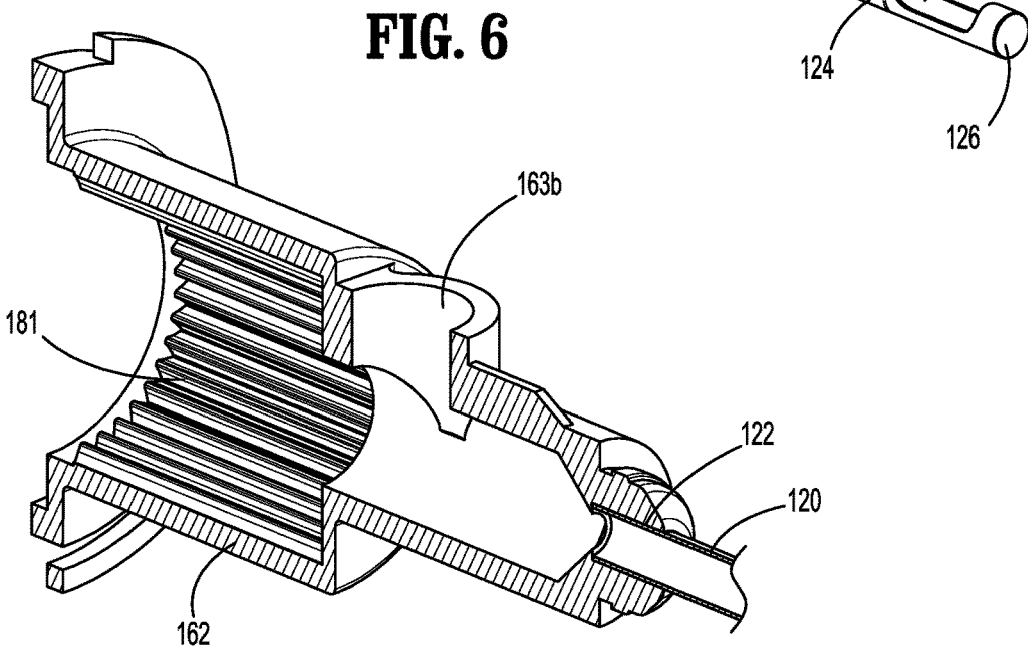
FIG. 7

TISSUE RESECTING INSTRUMENT

BACKGROUND

1. Technical Field

The present disclosure relates generally to the field of tissue resection. In particular, the present disclosure relates to a tissue resecting instrument configured to facilitate resection and removal of tissue from an internal surgical site, e.g., a uterus.

2. Background of Related Art

Tissue resection may be performed endoscopically within an organ, such as a uterus, by inserting an endoscope (or hysteroscope) into the uterus and passing a tissue resection instrument through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is an end effector assembly of a tissue-resecting device. The end effector assembly includes an outer shaft including a hub housing disposed about a proximal end portion thereof, an inner shaft disposed within and rotatable relative to the outer shaft and including a sun gear disposed about a proximal end portion thereof, and a drive assembly rotatably disposed within the hub housing.

The drive assembly includes a first driver rotatably disposed about the inner shaft distally of the sun gear, a second driver rotatably disposed about the inner shaft proximally of the sun gear, a plurality of planetary gears, and a locking clip. The plurality of planetary gears is radially disposed about the sun gear in meshed engagement therewith. Each planetary gear of the plurality of planetary gears is rotatably mounted on a post extending between the first and second drivers. The locking clip is positioned proximally of the plurality of planetary gears and the sun gear, rotationally keyed to the second driver, and engaged with the first driver via at least one snap-fit engagement to thereby retain the first and second drivers and the plurality of planetary gears in operable engagement with one another and the sun gear. As such, a rotational input provided to the second driver drives rotation of the first driver, the plurality of planetary gears, and the sun gear to thereby drive rotation of the inner shaft.

In an aspect of the present disclosure, the hub housing including a ring gear disposed on an interior surface thereof and each of the planetary gears of the plurality of planetary gears is disposed in meshed engagement with the ring gear.

In another aspect of the present disclosure, the rotational input provided to the second driver drives rotation of the inner shaft at an output speed different from an input speed of the rotational input.

In still another aspect of the present disclosure, a third driver or a portion thereof is slidably disposed about a portion of the second driver in fixed rotational orientation relative thereto such that rotation of the third driver provides the rotational input to the second driver.

In yet another aspect of the present disclosure, the first driver includes a helical channel defined therein and the hub housing includes a cam follower engaged within the helical channel such that the rotational input provided to the second driver drives rotation and reciprocation of the inner shaft.

In still yet another aspect of the present disclosure, the third driver is slidably disposed about the second driver in fixed rotational orientation relative thereto such that rotation of the third driver provides the rotational input to the second driver and such that the first and second drivers reciprocate relative to the third driver.

In another aspect of the present disclosure, the inner shaft includes a seal disposed about the proximal end thereof and configured to selectively contact the third driver to seal off the proximal end of the inner shaft as the second driver is reciprocated within the third driver.

In another aspect of the present disclosure, the outer shaft defines a window towards a closed distal end thereof and the inner shaft defines an open distal end. In such aspects, at least one of the windows of the outer shaft or the open distal end of the inner shaft may be surrounded by a cutting edge.

In another aspect of the present disclosure, a cap is engaged with the hub housing. Engagement of the cap with the hub housing retains an RFID chip within a pocket defined within the cap.

A method of assembling an end effector assembly of a tissue resecting instrument in accordance with aspects of the present disclosure includes obtaining an inner shaft including a sun gear disposed about a proximal end portion thereof, inserting a first driver about the inner shaft in a distal-to-proximal direction to a position distally of the sun gear, and coupling a plurality of planetary gears to the sun gear such that the plurality of planetary gears is radially disposed about and in meshed engagement with the sun gear proximally of the first driver. The method further includes inserting a second driver about the inner shaft in a proximal-to-distal direction to a position proximally of the sun gear and the plurality of planetary gears, and positioning a locking clip proximally adjacent the sun gear and the plurality of planetary gears and engaging the locking clip with the first driver such that a portion of the second driver is disposed therebetween, thereby retaining the first and second drivers and the plurality of planetary gears in operable engagement with one another and the sun gear.

In an aspect of the present disclosure, the method further includes obtaining an outer shaft including at least a portion of a hub housing disposed about a proximal end portion thereof, and inserting the inner shaft, including the first and second drivers, the plurality of planetary gears, and the locking clip disposed thereon in operable engagement with one another and the sun gear, in a proximal-to-distal direction into the at least a portion of a hub housing and such that the inner shaft extends through the outer shaft.

In another aspect of the present disclosure, inserting the inner shaft further includes coupling the plurality of planetary gears in meshed engagement with a ring gear disposed within the hub housing.

In still another aspect of the present disclosure, the method further includes engaging a cam follower with the hub housing such that the cam follower extends into the hub housing to engage a helical channel defined within the first driver therein.

In yet another aspect of the present disclosure, the method further includes coupling a third driver to the second driver in slidable, rotationally fixed engagement.

In still yet another aspect of the present disclosure, the method further includes positioning a lockout cap about the third driver and engaging the lockout cap with the hub housing. In such aspects, positioning the lockout cap about the third driver and engaging the lockout cap with the hub housing may releasably lock the inner shaft in position relative to the outer shaft. Additionally or alternatively, positioning the lockout cap about the third driver and engaging the lockout cap with the hub housing may capture an RFID chip within a pocked defined within the lockout cap.

In another aspect of the present disclosure, engaging the locking clip with the first driver includes at least one snap-fit engagement.

BRIEF DESCRIPTION OF THE DRAWINGS

Various aspects and features of the present disclosure are described hereinbelow with reference to the drawings wherein like numerals designate identical or corresponding elements in each of the several views.

FIG. 1 is a side, perspective view of an end effector assembly of a tissue resecting instrument provided in accordance with aspects of the present disclosure wherein an inner shaft of the end effector assembly is disposed in a first position;

FIG. 2 is an enlarged, perspective view of the area of detail indicated as "2" in FIG. 1;

FIG. 3 is an enlarged, perspective view of a distal end portion of the end effector assembly of FIG. 1, wherein the inner shaft of the end effector assembly is disposed in a second position;

FIG. 5 is an enlarged, side, perspective view of the area of detail indicated as "5" in FIG. 4;

FIG. 6 is an enlarged, side, perspective view of an outer shaft of the end effector assembly of FIG. 1, including a distal body portion of a hub housing of a hub assembly assembled thereon and a follower assembly of the hub assembly shown exploded from the distal body portion;

FIG. 7 is a longitudinal, cross-sectional view of the distal body portion of the hub housing of FIG. 6 including the outer shaft engaged thereto;

DETAILED DESCRIPTION

Figure 23:
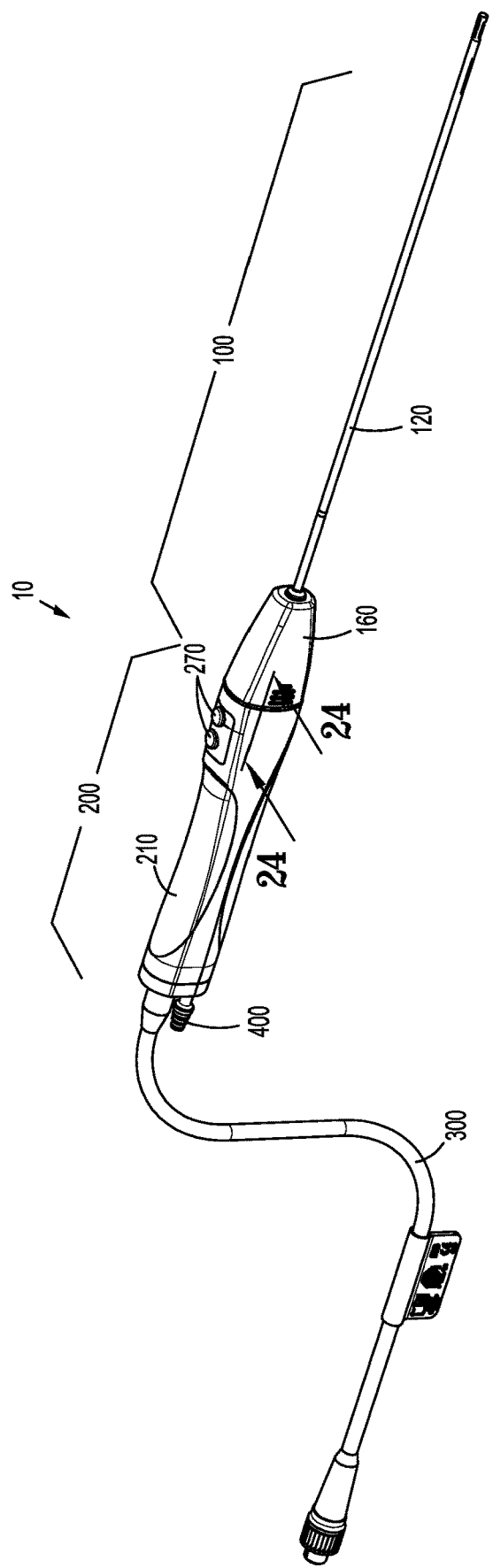
FIG. 23 is a side, perspective view of a tissue resecting instrument including the end effector assembly of FIG. 1 engaged with a handpiece.

Referring generally to FIGS. 1 and 23, a tissue resecting instrument 10 provided in accordance with the present disclosure and configured to resect tissue includes an end effector assembly 100 and a handpiece assembly 200. Tissue resecting instrument 10 is adapted to connect to a control unit (not shown) via a cable 300 to provide power and control functionality to tissue resecting instrument 10, although tissue resecting instrument 10 may alternatively or additionally include a power source, e.g., battery, and/or a control unit disposed within handpiece assembly 200. Tissue resecting instrument 10 is further adapted to connect to a fluid management system (not shown) via outflow tubing (not shown) connected to outflow port 400 for applying suction to remove fluid, tissue, and debris from a surgical site via tissue resecting instrument 10. The control unit and fluid management system may be integral with one another, coupled to one another, or separate from one another.

Tissue resecting instrument 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In any of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for interchangable use of different end effector assemblies, e.g., different length, configuration, etc., end effector assemblies, with handpiece assembly 200.

Figure 4:
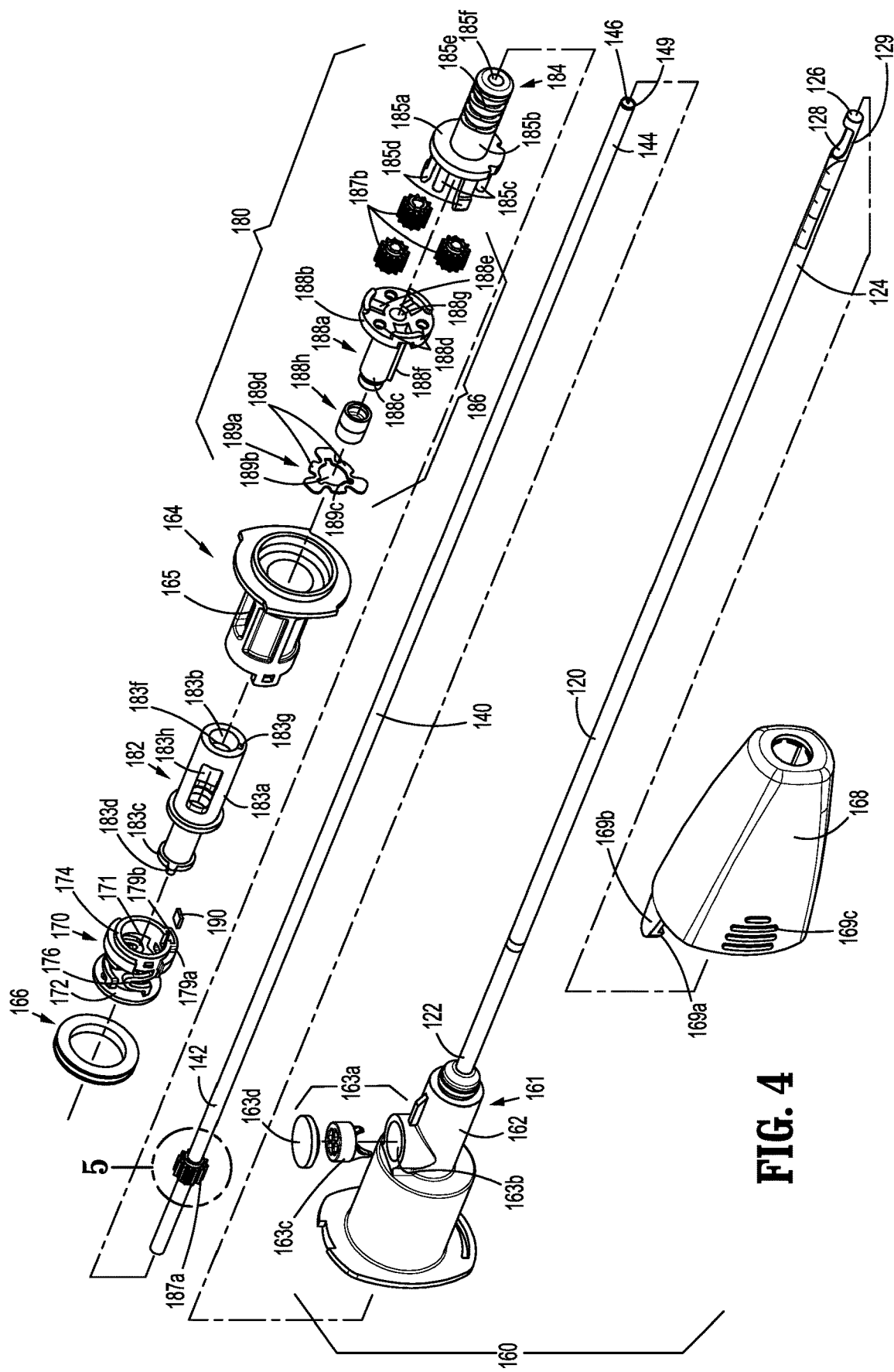
FIG. 4 is a side, perspective, exploded view of the end effector assembly of FIG. 1.

Continuing with reference to FIG. 1, end effector assembly 100 includes an outer shaft 120, an inner shaft 140, a hub assembly 160, a drive assembly 180 (FIG. 4), and an RFID chip 190 (FIG. 4). Referring also to FIGS. 2 and 3, outer shaft 120 includes a proximal end portion 122 (FIG. 4) and a distal end portion 124 defining an at least partially closed distal end 126 and a transverse window 128 disposed adjacent the at least partially closed distal end 126. Window 128 provides access to the interior of outer shaft 120 transversely through a sidewall thereof and may be surrounded by a cutting edge 129 about the outer perimeter of window 128 so as to facilitate cutting of tissue passing through window 128 and into outer shaft 120.

Inner shaft 140 is translationally and rotatably disposed within outer shaft 120 and includes a proximal end portion 142 (FIG. 4) and a distal end portion 144 defining an open distal end 146. A cutting edge 149 may surround the outer perimeter of open distal end 146 so as to facilitate cutting of tissue passing through open distal end 146 and into inner shaft 140.

Referring still to FIGS. 1-3, inner shaft 140 is configured for translation and rotation within and relative to outer shaft 120 to thereby rotate and translate open distal end 146 relative to window 128. More specifically, inner shaft 140 is configured to rotate and translate between a first position (FIG. 2), wherein open distal end 146 is disposed at or proximally of a proximal end of window 128, through a second position (FIG. 3), wherein open distal end 146 is disposed within window 128, to a third position (not shown), wherein open distal end 146 is disposed at or distally of a distal end of window 128. The rotation of inner shaft 140 and, thus, cutting edge 149 thereof, facilitates the cutting of tissue as inner shaft 140 is translated between the first, second, and third positions. Suction is applied trough inner shaft 140, as detailed below, to facilitate removal of the cut tissue, fluids, and debris through inner shaft 140.

Inner shaft 140 is configured to continuously rotate and translate from the first position (FIG. 2) through the second position (FIG. 3) to the third position and back from the third position to the first position (FIG. 2) though the second position (FIG. 3). Other suitable configurations of outer shaft 120 and/or inner shaft 140 that cooperate to facilitate tissue cutting are also contemplated, such as those employing reciprocation, rotation, and/or oscillation of inner shaft 140 relative to outer shaft 120.

With reference to FIGS. 1 and 4, as noted above, end effector assembly 100 includes outer shaft 120, inner shaft 140, a hub assembly 160, and a drive assembly 180. End effector assembly 100 further includes an RFID chip 190 captured between a lockout cap 170 of hub assembly 160 and a proximal extension portion 164 of a hub housing 161 of hub assembly 160, as detailed below.

Figure 24:
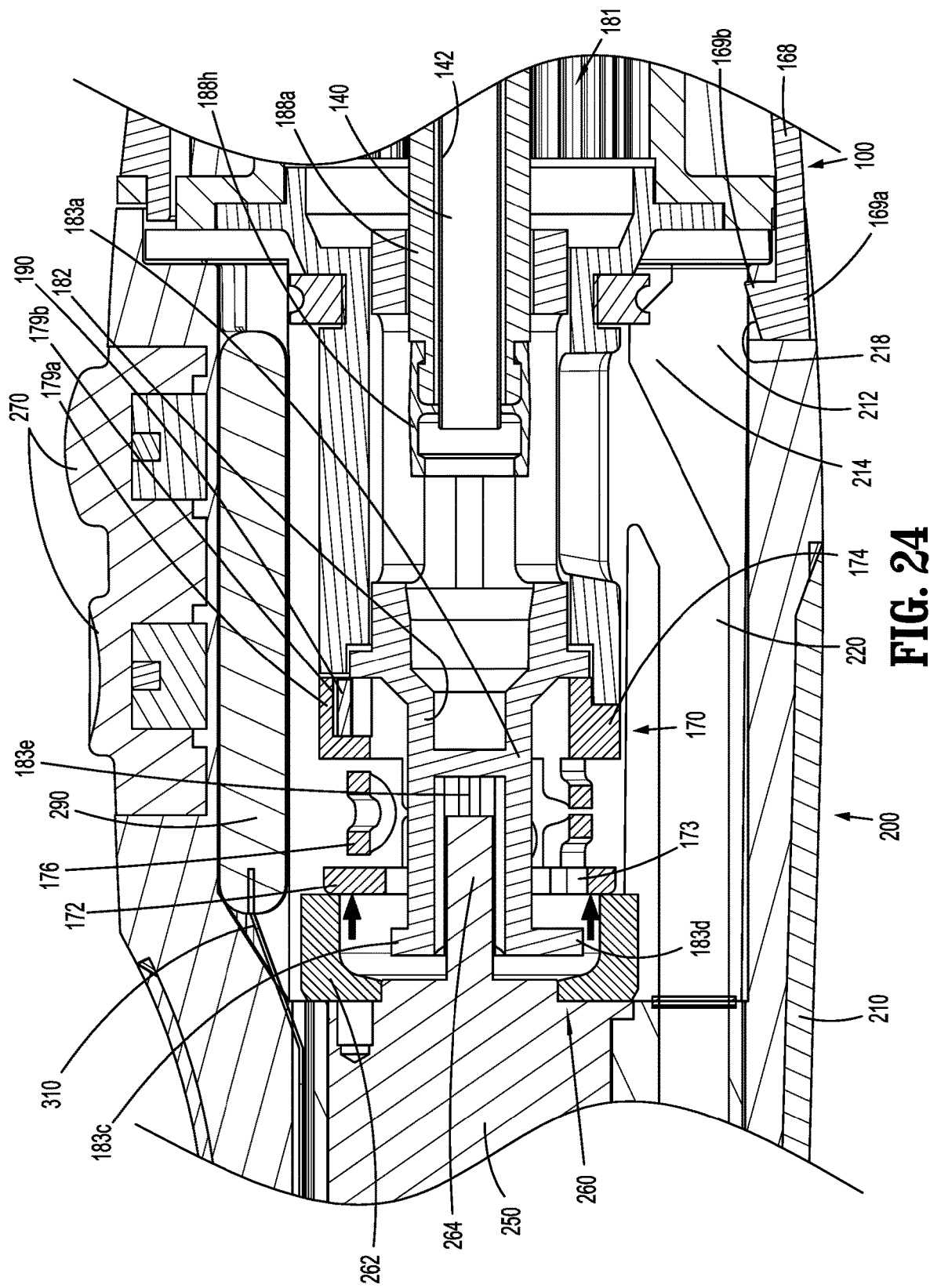
FIG. 24 is a longitudinal, cross-sectional view taken across section line "24-24" of FIG. 23.

Hub assembly 160 includes a hub housing 161 having a distal body portion 162 and a proximal extension portion 164 that are configured for engagement with one another, e.g., via snap-fitting or other suitable engagement. Referring momentarily to FIGS. 23 and 24, with end effector assembly 100 engaged with handpiece assembly 200, proximal extension portion 164 of hub housing 161 extends into handpiece assembly 200 while distal body portion 162 substantially abuts and extends distally from handpiece assembly 200. Proximal extension portion 164 of hub housing 161 further defines an outflow opening 165 through a sidewall thereof that is configured to fluidly communicate with an internal bore 214 of handle housing 210 of handpiece assembly 200 when end effector assembly 100 is engaged therewith.

Returning to FIGS. 1 and 4, and with additional reference to FIGS. 6 and 7, distal body portion 162 of hub housing 161 is fixedly disposed about proximal end portion 122 of outer shaft 120 with outer shaft 120 extending distally therefrom. Inner shaft 140 extends through outer shaft 120, as noted above, and extends proximally through distal body portion 162 of hub housing 161 into proximal extension portion 164 of hub housing 161 wherein drive assembly 180 is operably coupled to proximal end portion 142 of inner shaft 140. Distal body portion 162 of hub housing 161 further defines an elongated ring gear 181 on an interior cylindrical surface thereof.

A follower assembly 163a of hub assembly 160 is seated within a transverse aperture 163b defined through distal body portion 162 of hub housing 161. Follower assembly 163a includes a cam follower 163c and a cap 163d configured to retain cam follower 163c within transverse aperture 163b such that cam follower 163c extends into the interior of distal body portion 162 of hub housing 161.

Figure 10:
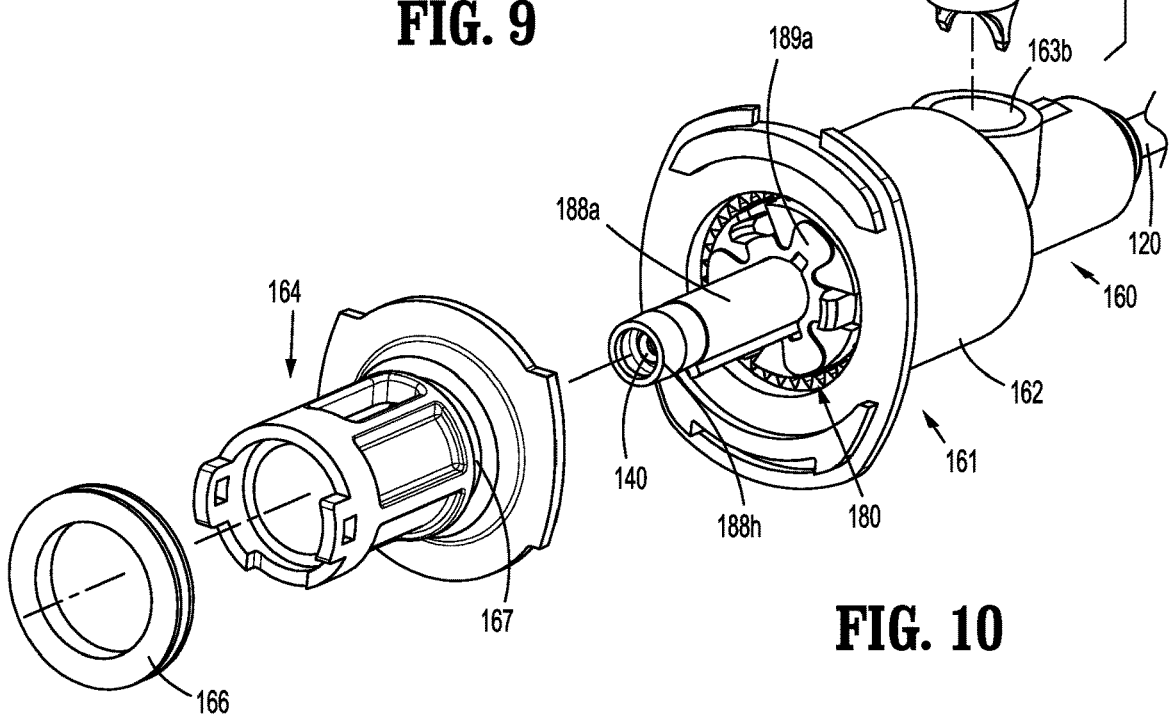
FIG. 10 is a rear, perspective view of the portion of the end effector assembly of FIG. 1 as illustrated in FIG. 6 further including the inner shaft, having the gear assembly assembled thereon, disposed therein and a proximal extension of the hub housing and an O-ring shown exploded therefrom.
Figure 11:
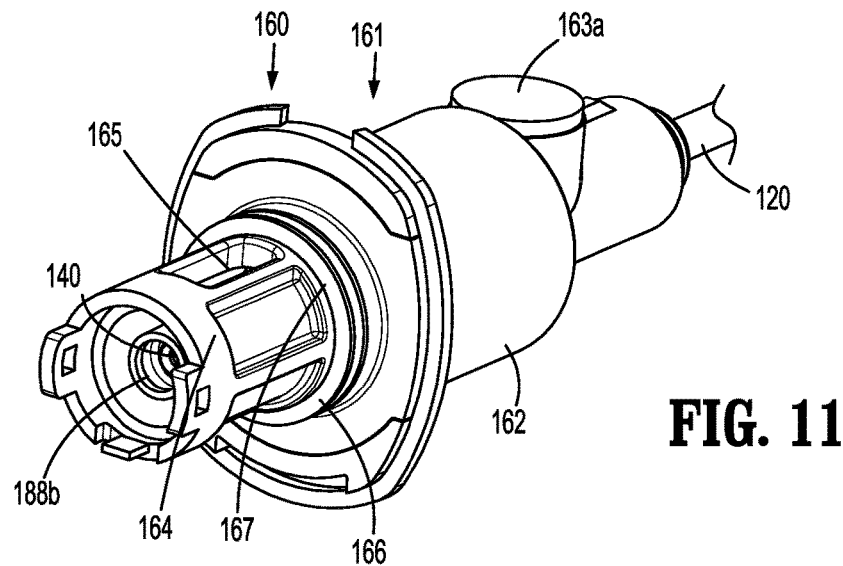
FIG. 11 is a rear, perspective view of the portion of the end effector assembly of FIG. 1 as illustrated in FIG. 10 with the proximal extension of the hub housing and the O-ring assembled thereon.

As illustrated in FIGS. 10 and 11, hub assembly 160 further includes an O-ring 166 configured for engagement about proximal extension portion 164 of hub housing 161 distally of outflow opening 165. O-ring 166, as illustrated in FIG. 24, is configured to establish a fluid-tight seal against the interior of handle housing 210 of handpiece assembly 200 when end effector assembly 100 is engaged therewith to inhibit fluid from travelling distally after exiting outflow opening 165.

With reference to FIGS. 4 and 16-18, hub assembly 160 additionally includes an outer shell 168 configured for positioning about distal body portion 162 of hub housing 161 and for engagement therewith, e.g., via snap-fit engagement or in any other suitable manner. A cantilever engagement finger 169a extends proximally from a lower surface of outer shell 168 of hub housing 161 and proximally from distal body portion 162 of hub housing 161 when outer shell 168 is engaged thereabout. Engagement finger 169a includes an engagement tooth 169b extending therefrom that is configured for engagement within a corresponding aperture 218 defined within handle housing 210 of handpiece assembly 200 (see FIG. 24) to enable releasable engagement of end effector assembly 100 with handpiece assembly 200 (FIG. 24). Grasping ribs 169c are defined on side surfaces of outer shell 168 to facilitate engagement and disengagement of end effector assembly 100 to and from handpiece assembly 200 (FIG. 24).

Referring to FIGS. 4, 13-15, 21, and 22, lockout cap 170 of hub assembly 160 is configured for snap-fit or other suitable engagement with a proximal end portion of proximal extension portion 164 of hub housing 161. Lockout cap 170 defines a longitudinal lumen 171 extending therethrough and includes a proximal stop ring 172, a distal stop ring 174 rotationally fixed relative to proximal stop ring 172, and a biasing member 176 disposed between proximal and distal stop rings 172, 174, respectively. Proximal stop ring 172 defines a recess 173 oriented radially inwardly towards longitudinal lumen 171.

Distal stop ring 174 is fixed relative to proximal extension portion 164 of hub housing 161, e.g., via snap-fit engagement between distal stop ring 174 and proximal extension portion 164. Distal stop ring 174 further includes an external collar 179a defining a pocket 179b. Pocket 179b is configured to receive RFID chip 190 therein. When lockout cap 170 is engaged with proximal extension portion 164, e.g., via snap-fitting, the open end of pocket 179b is blocked by a proximal face of proximal extension portion 164, thereby capturing RFID chip 190 therein.

Biasing member 176 may be a living hinge formed integrally with proximal and distal stop rings 172, 174, respectively, e.g., formed as a single molded component, although biasing member 176 may alternatively be formed separately from either or both of proximal and distal stop rings 172, 174, respectively, and/or may be any other suitable biasing member such as, for example, a compression spring. Biasing member 176 is configured to bias proximal stop ring 172 proximally away from distal stop ring 174, corresponding to an at-rest position of lockout cap 170.

Referring to FIGS. 4, 5, 8, 9, and 18, drive assembly 180 is configured to operably couple drive rotor 260 of handpiece assembly 200 (see FIG. 24) with inner shaft 140 such that rotation of drive rotor 260 (FIG. 24) drives rotation and reciprocation of inner shaft 140 within and relative to outer shaft 120. Drive assembly 180, more specifically, includes a proximal driver 182, a distal driver 184, and a gear assembly 186 disposed between and operably coupling proximal and distal drivers 182, 184, respectively, with one another. Proximal driver 182 is configured to receive a rotational input from drive rotor 260 (FIG. 24), gear assembly 186 is configured to amplify or attenuate the output rotation of inner shaft 140 relative to the input rotation from drive rotor 260 (FIG. 24), and distal driver 184 is configured to impart the amplified or attenuated output rotation to inner shaft 140 as well as to reciprocate inner shaft 140.

Figure 12:
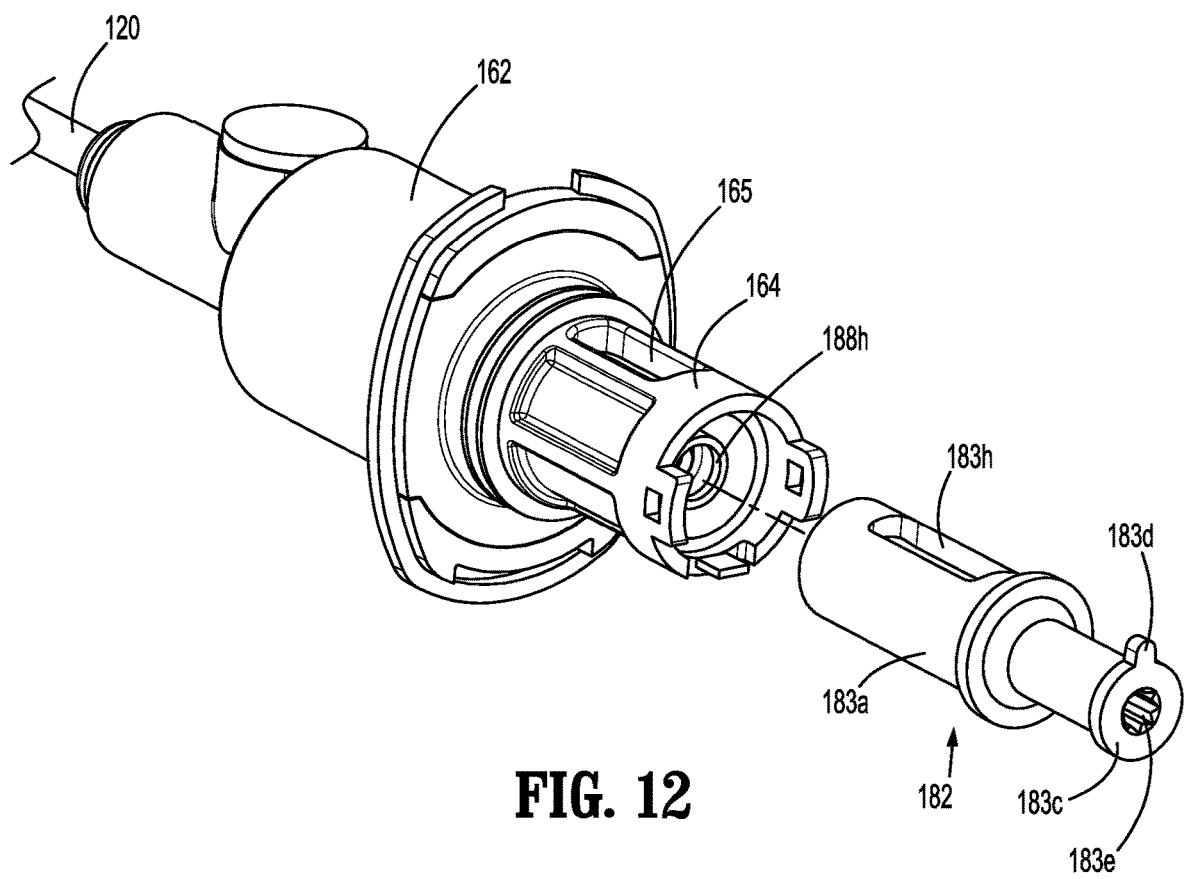
FIG. 12 is a rear, perspective view of the portion of the end effector assembly of FIG. 1 as illustrated in FIG. 11 with a proximal driver of the drive assembly shown exploded therefrom.
Figure 13:
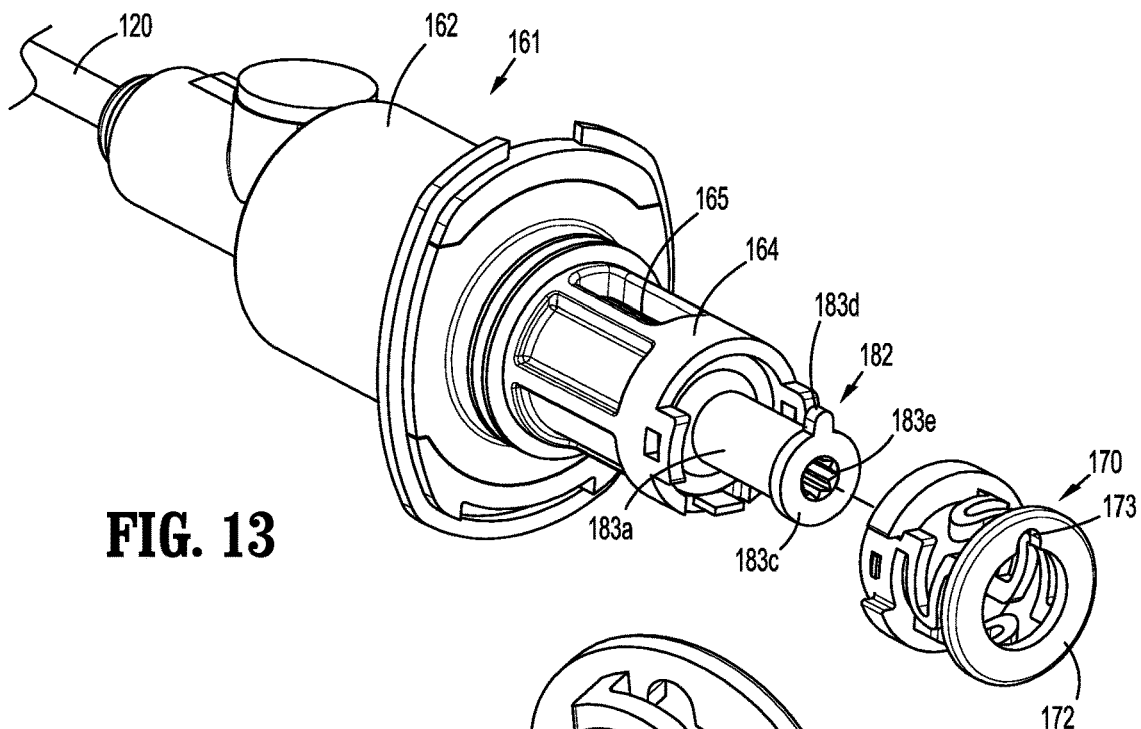
FIG. 13 is a rear, perspective view of the portion of the end effector assembly of FIG. 1 as illustrated in FIG. 12 with the proximal driver assembled thereon and a lockout cap shown exploded therefrom.

With additional reference to FIGS. 12 and 13, proximal driver 182 of drive assembly 180 includes a generally cylindrical body 183a defining a lumen 183b extending longitudinally therethrough. Body 183a includes an external collar 183c disposed annularly thereabout at a proximal end portion thereof. External collar 183c includes a radially-outwardly extending tab 183d. Body 183a further includes a proximally-facing cavity 183e at least a portion of which has a non-circular cross-sectional configuration, e.g., an 8-point star or other polygonal configuration, that is configured to at least partially receive drive rotor 260 of handpiece assembly 200 in fixed rotational orientation (see FIG. 24). Body 183a additionally defines a distally-facing cavity 183f including a longitudinally-extending channel 183g defined within an inwardly-facing surface of body 183a. A longitudinally-extending slot 183h defined through a side wall of body 183a communicates with distally-facing cavity 183f to define a flow path therethrough, e.g., from within distally-facing cavity 183f to externally of body 183a.

Turning to FIGS. 4, 8, 9, and 18, distal driver 184 of drive assembly 180 includes a proximal plate 185a and a distal cylindrical body 185b extending distally from proximal plate 185a. Proximal plate 185a includes a plurality, e.g., three, posts 185c extending proximally therefrom and arranged radially about a longitudinal axis defined through distal driver 184. Proximal plate 185a further includes a plurality of engagement arms 185d arranged radially about the longitudinal axis of distal driver 184 and extending proximally from outer peripheral edges of proximal plate 185a.

Distal cylindrical body 185b of distal driver 184 defines a helical channel 185e about the outer annular periphery thereof. Helical channel 185e includes forward and reverse channel portions (defining similar or different pitches) blended at their ends to define a continuous helical channel 185e. Helical channel 185e is configured to receive cam follower 163c of cam assembly 163a therein such that as distal driver 184 is driven to rotate, the engagement of cam follower 163c within helical channel 185e reciprocates distal driver 184, e.g., distally while cam follower 163c is disposed within the forward channel portion of helical channel 185e, proximally while cam follower 163c is disposed within the reverse channel portion of helical channel 185e, and changing directions when cam follower 163c is disposed at the blended ends of helical channel 185e. Distal driver 184 further includes a longitudinally-extending lumen 185f defined therethrough.

Continuing with reference to FIGS. 4, 8, 9, and 18, and with additional reference to FIG. 5, gear assembly 186 includes a sun gear 187a fixedly engaged about proximal end portion 142 of inner shaft 140, a plurality of, e.g., three, planetary gears 187b, an intermediate driver 188a, and a locking clip 189a.

Planetary gears 187b are rotatably mounted on posts 185c of proximal plate 185a of distal driver 184 and disposed in meshed engagement about sun gear 187a. More specifically, proximal end portion 142 of inner shaft 140 extends through longitudinally-extending lumen 185f of distal driver 184 with sun gear 187a disposed proximally of distal driver 184 to enable sun gear 187a to mesh with planetary gears 187b. Planetary gears 187b are configured for slidable, meshed engagement with elongated ring gear 181 of distal body portion 162 of hub housing 161 (see FIGS. 7, 10 and 18).

Intermediate driver 188a includes a distal plate 188b and a proximal cylindrical body 188c extending proximally from distal plate 188b. Distal plate 188b defines a plurality of apertures 188d arranged radially about a longitudinal axis defined therethrough. Each apertures 188d is configured to receive one of the posts 185c of distal driver 184 to rotatably mount and retain planetary gears 187b between intermediate driver 188a and distal driver 184. Distal plate 188b further includes a plurality of, e.g., three, slots 188e at outer peripheral edges thereof that are each configured to receive one of the engagement arms 185d of distal driver 184 therethrough.

Proximal cylindrical body 188c of intermediate driver 188a defines a longitudinally-extending rail 188f protruding from and extending along an outer peripheral surface thereof. Proximal cylindrical body 188c is configured for receipt within distally-facing cavity 183f of body 183a of proximal driver 182, with longitudinally-extending rail 188f slidably received within longitudinally-extending channel 183g of proximal driver 182 to rotationally lock proximal driver 182 and intermediate driver 188a with one another. Intermediate driver 188a further includes a longitudinally-extending lumen 188g defined therethrough that communicates with longitudinally-extending lumen 185f of distal driver 184. Further, an elastomeric seal 188h is engaged about a proximal end of proximal cylindrical body 188c of intermediate driver 188a, extending about lumen 188g. Seal 188h may be resiliently retained about the proximal end of proximal cylindrical body 188c, e.g., via the elastomeric material forming seal 188h, or may be secured thereto in any other suitable manner.

Figure 9:
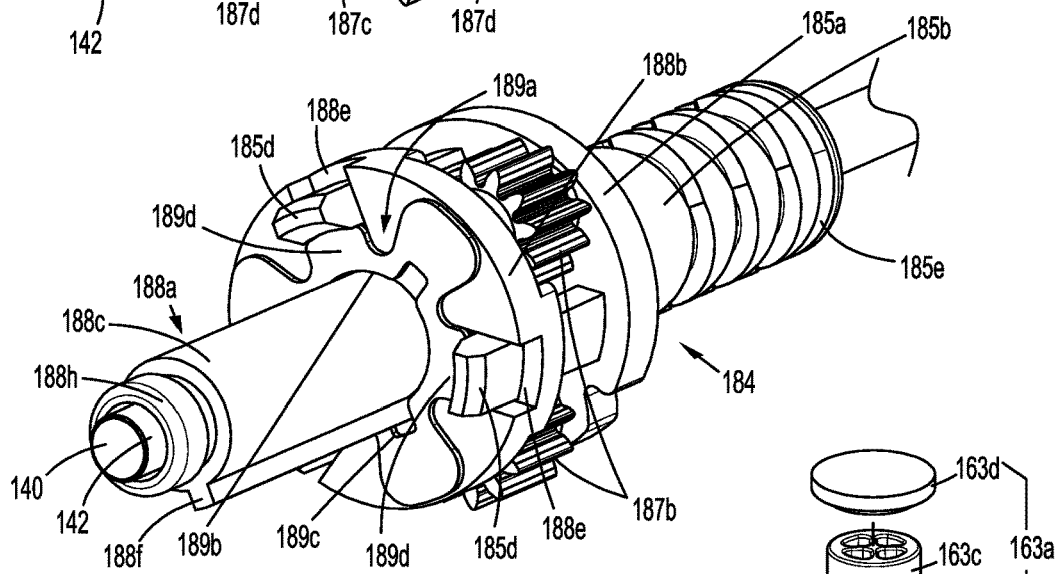
FIG. 9 is a rear, perspective view of the proximal end portion of the inner shaft including the gear assembly fully assembled thereon.

Locking clip 189a, as illustrated in FIGS. 4 and 9, is configured for positioning about proximal cylindrical body 188c of intermediate driver 188a, proximally adjacent distal plate 188b of intermediate driver 188a. Locking clip 189a, more specifically, defines central opening 189b configured to receive proximal cylindrical body 188c of intermediate driver 188a and a notch 189c defined within the annular interior edge of locking clip 189a that defines central opening 189b for receipt of longitudinally-extending rail 188f therein. Locking clip 189a further includes a plurality of, e.g., three, lock tabs 189d each configured to engage one of the engagement arm 185d of distal driver 184 to thereby engage locking clip 189a with distal driver 184, retaining planetary gears 187b and intermediate driver 188a therebetween.

With reference to FIGS. 5-17, the assembly of end effector assembly 100 is detailed. As illustrated in respective FIGS. 5 and 6, pre-assembly of sun gear 187a about proximal end portion 142 of inner shaft 140 in fixed relation relative thereto and pre-assembly of distal body portion 162 of hub housing 161 about proximal end portion 122 of outer shaft 120 in fixed relation relative thereto, is accomplished.

Figure 8:
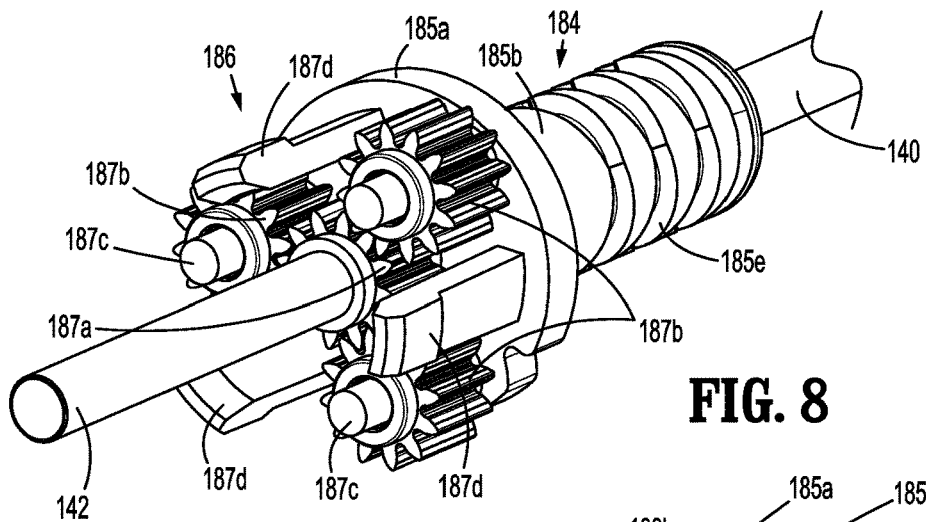
FIG. 8 is a rear, perspective view of a proximal end portion of the inner shaft of the end effector assembly of FIG. 1 including a portion of a gear assembly of a drive assembly assembled thereon.

Referring to FIGS. 8 and 9, once the above-detailed pre-assembly of sun gear 187a about proximal end portion 142 of inner shaft 140 is complete, distal driver 184 and gear assembly 186 are installed about inner shaft 140. More specifically, distal driver 184 is slid proximally over inner shaft 140 until posts 185c surround sun gear 187a. Thereafter, planetary gears 187b are disposed on posts 185c in mesh engagement with sun gear 187a. Next, intermediate driver 188a is slid distally over inner shaft 140 until the free ends of posts 185 are received within apertures 188d of distal plate 188b of intermediate driver 188a and engagement arms 185d extend proximally through slots 188e.

With gear assembly 186 assembled as noted above, locking clip 189a is slid distally about intermediate driver 188a, in fixed rotational engagement therewith (via the receipt of longitudinally-extending rail 188f within notch 189c), into abutment with distal plate 188b of intermediate driver 188a wherein engagement arms 185d of distal driver 184 engage, e.g., in snap-fit engagement, lock tabs 189d of locking clip 189a to thereby operably couple drive assembly 180 (with the exception of proximal driver 182) about inner shaft 140. At this point or prior thereto, seal 188h is engaged, e.g., resiliently retained, about the proximal end of intermediate driver 188a.

Referring to FIG. 10, inner shaft 140, including drive assembly 180 (with the exception of proximal driver 182) operably engaged thereabout, is inserted, in a proximal-to-distal direction, through distal body portion 162 of hub hosing 161 and outer shaft 120 such that planetary gears 187b are disposed in slidable, meshed engagement with elongated ring gear 181. Thereafter, follower assembly 163a is installed within distal body portion 162 of hub housing 161 via first inserting cam follower 163c through transverse aperture 163b of distal body portion 162 of hub housing 161 and thereafter installing cap 163d within transverse aperture 163b to retain cam follower 163c within transverse aperture 163b and in engagement within helical channel 185e.

With additional reference to FIG. 11, proximal extension portion 164 of hub housing 161 is slid, in a proximal-to-distal direction, about intermediate driver 188a, and into engagement, e.g., via snap-fitting, with distal body portion 162 of hub housing 161. Prior to or after the engagement of proximal extension portion 164 with distal body portion 162, O-ring 166 is slid in a proximal-to-distal direction about proximal extension portion 164 of hub housing 161 to be seated within an annular recess 167 defined about proximal extension portion 164 of hub housing 161 distally of outflow opening 165. Next, proximal driver 182 is inserted through distal body portion 162 of hub housing 161 and about intermediate driver 188a in rotationally-fixed orientation relative to intermediate driver 188a, e.g., via receipt of longitudinally-extending rail 188f within longitudinally-extending channel 183g.

Figure 14:
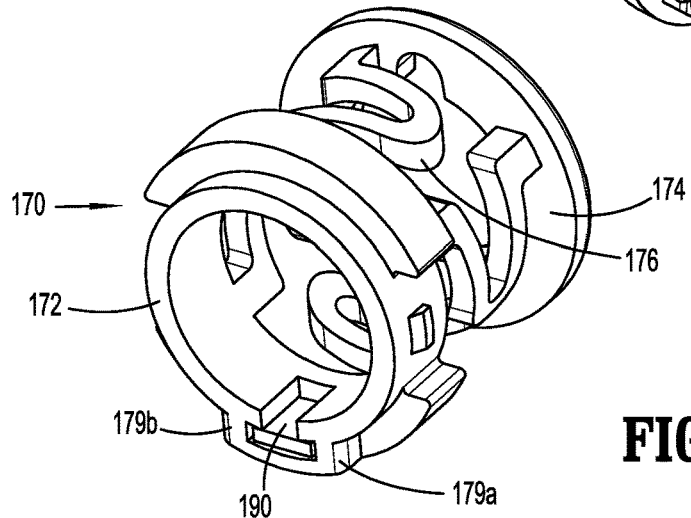
FIG. 14 is a perspective view of the lockout cap of FIG. 13.
Figure 15:
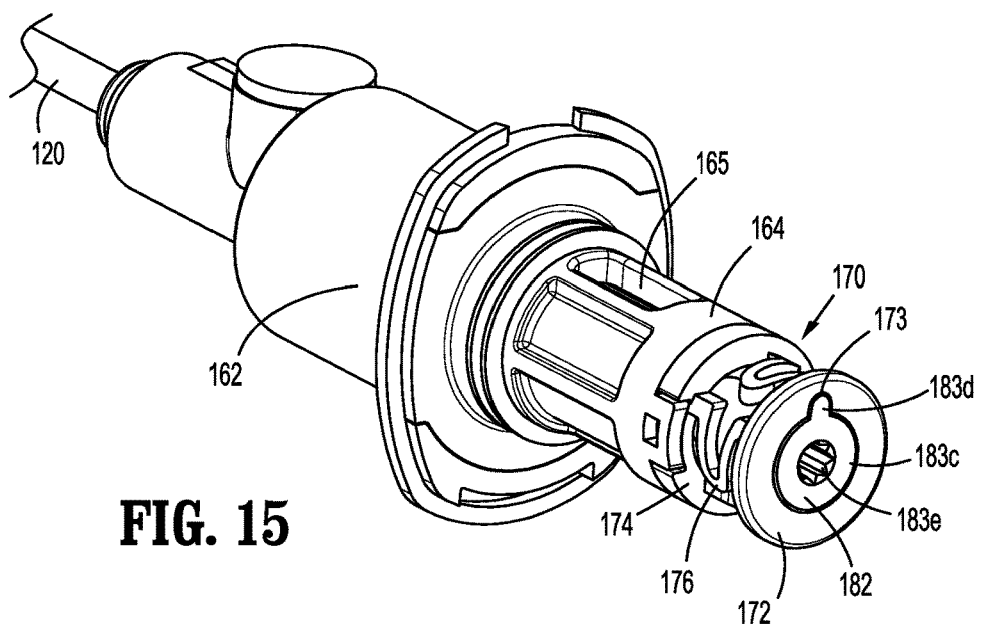
FIG. 15 is a rear, perspective view of the portion of the end effector assembly of FIG. 1 as illustrated in FIG. 13 with the lockout cap assembled thereon.
Figure 16:
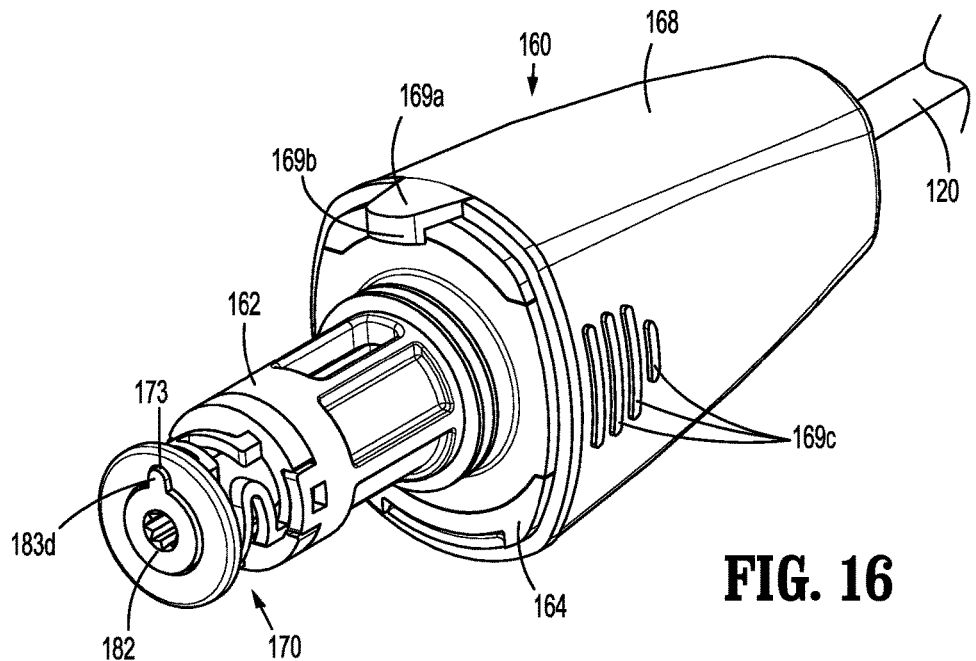
FIG. 16 is a rear, perspective view of a proximal end portion of the end effector assembly of FIG. 1 in an assembled condition.

Referring to FIGS. 13-15, RFID chip 190 is loaded into pocket 179b of lockout cap 170 and, thereafter, lockout cap 170 is slid in a proximal-to-distal direction about proximal driver 182 into engagement, e.g., via snap-fitting, with proximal extension portion 164 of hub housing 161. Lockout cap 170, when engaged with proximal extension portion 164 of hub housing 161, inhibits proximal driver 182 from passing proximally therethrough. Further, radially-outwardly extending tab 183d of proximal driver 182 is received within recess 173 of proximal stop ring 172 of lockout cap 170 upon engagement of lockout cap 170 with proximal extension portion 164 of hub housing 161 and, while proximal stop ring 172 remains in the initial position under the bias of biasing member 176, lockout cap 170 retains proximal driver 182 in rotationally-fixed orientation relative to hub housing 161, thus retaining inner shaft 140 in fixed position relative to outer shaft 120.

Figure 17:
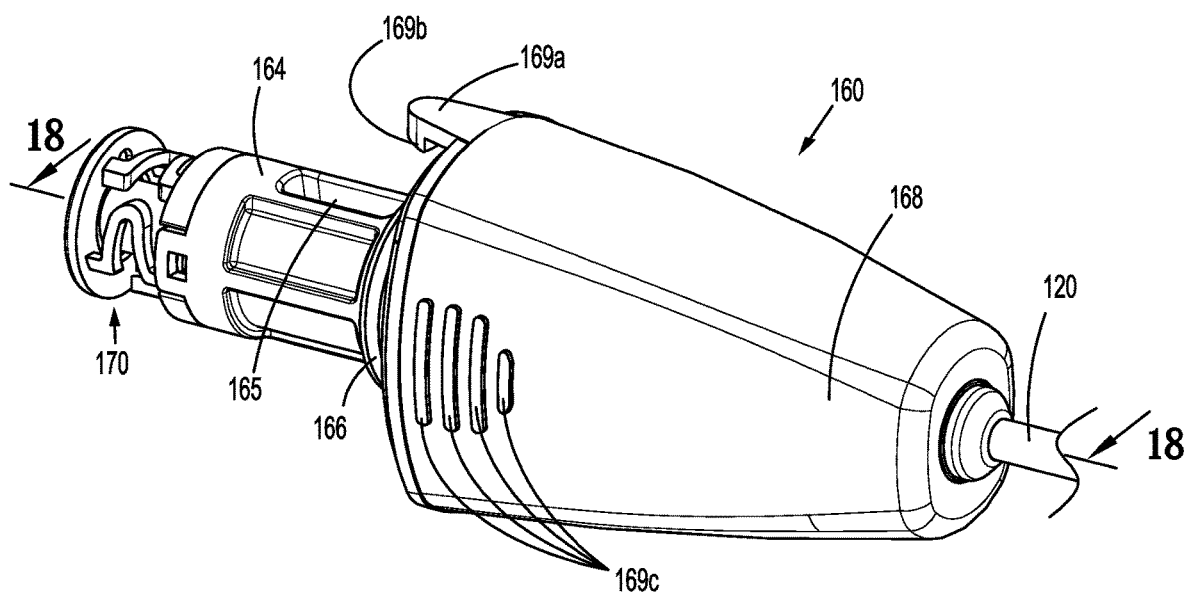
FIG. 17 is a side, perspective view of the proximal end portion of the end effector assembly of FIG. 1 in the assembled condition.
Figure 18:
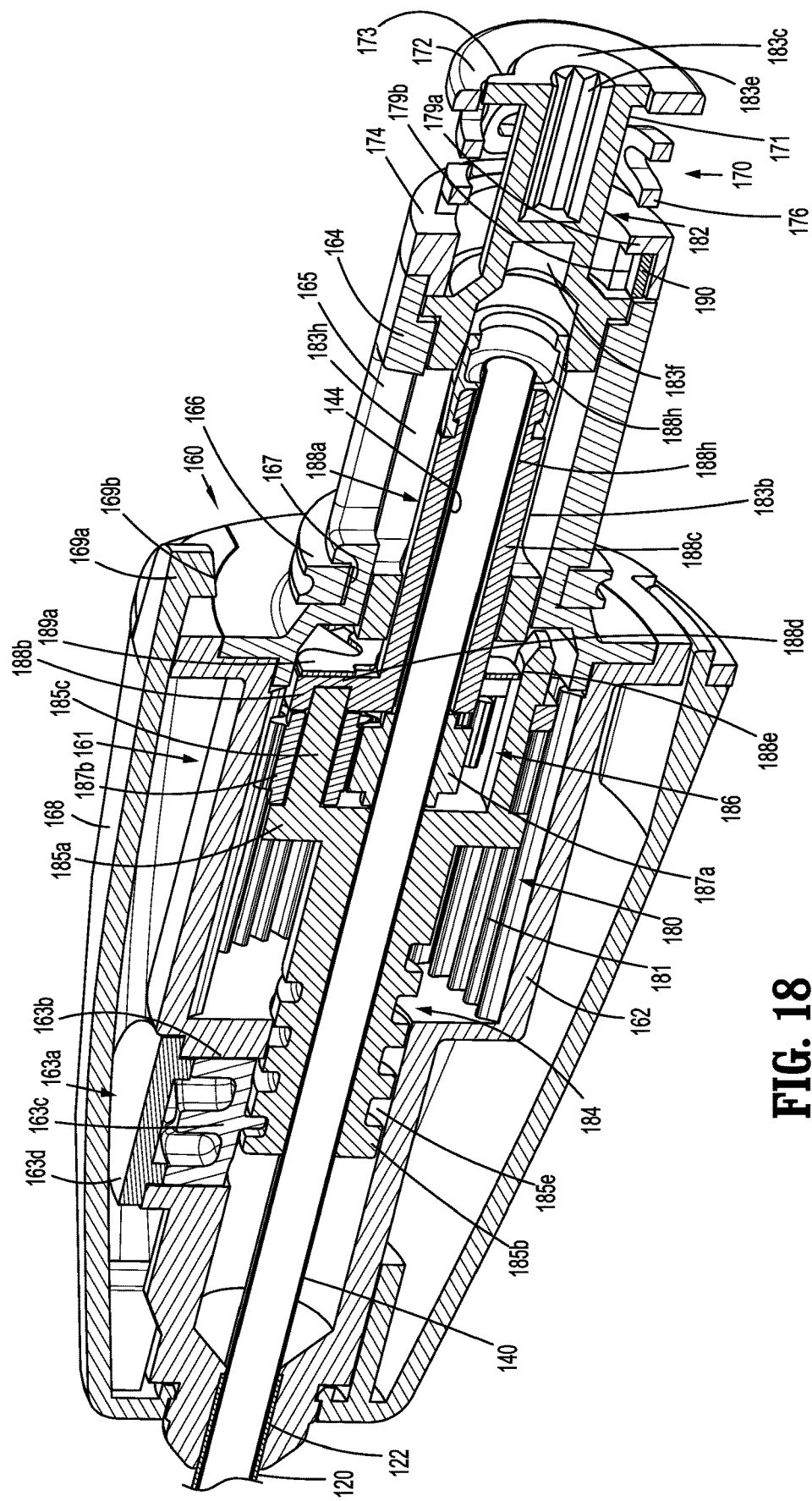
FIG. 18 is a perspective, longitudinal, cross-sectional view taken across section line "18-18" of FIG. 17.

Turning to FIGS. 17 and 18, outer shell 168 is slid in a distal-to-proximal direction about outer shaft 120 and distal body portion 162 of hub housing 161 into engagement, e.g., via snap-fitting, with distal body portion 162 of hub housing 161 to complete the assembly of end effector assembly 100 (FIG. 1). In the fully assembled condition of end effector assembly 100 (FIG. 1), as noted above, biasing member 176 biases proximal stop ring 172 proximally such that proximal driver 182 is engaged with lockout cap 170 in rotationally fixed orientation. End effector assembly 100, e.g., drive assembly 180 and lockout cap 170, may be configured such that, in this rotationally locked position, inner shaft 140 is disposed in the third position relative to outer shaft 120, wherein open distal end 146 of inner shaft 140 is disposed at or distally of the distal end of window 128 of inner shaft 120 (See FIGS. 1-3). Other configurations are also contemplated.

Referring to FIGS. 1, 23, and 24, handpiece assembly 200 generally includes handle housing 210, an outflow path 220 defined through handle housing 210 and communicating with an outflow port 400, a motor 250 disposed within handle housing 210, and drive rotor 260 disposed within handle housing 210 and operably coupled to motor 250. Handpiece assembly 200 may further include one or more controls 270, e.g., buttons, disposed on handle housing 210 to facilitate activation of tissue resecting instrument 10, toggle between various modes, and/or to vary the speed of motor 250. Further, outflow tubing (not shown) is configured to connect to outflow port 400 to thereby connect outflow port 400 to a fluid management system (not shown). The fluid management system includes a vacuum source to establish suction through tissue resecting instrument 10 and the outflow tubing to facilitate removal of fluid, tissue, and debris from the surgical site and may also include a collection reservoir, e.g., a collection canister, for collecting the removed fluid, tissue, and debris. As an alternative or in addition to a vacuum source establishing suction through tissue resecting instrument 10 and the outflow tubing, vacuum may be created therethrough via a pressure differential between the surgical site and the outflow path.

Handle housing 210 defines a pencil-grip configuration, although other configurations are also contemplated, e.g., pistol-grip configurations, and includes an open distal end portion 212 communicating with an internal bore 214. Open distal end portion 212 of handle housing 210 provides access to drive rotor 260 and internal bore 214 within handle housing 210 such that, upon engagement of end effector assembly 100 with handpiece assembly 200, as detailed below, a portion of end effector assembly 100 extends through open distal end portion 212 and into internal bore 214 to operably couple with drive rotor 260 and fluidly couple end effector assembly 100 with internal bore 214 and, thus, outflow path 220.

Cable 300 extends proximally from handle housing 210 and is configured to connect to the control unit (not shown) to provide power and control functionality to tissue resecting instrument 10. Cable 300, more specifically, houses one or more wires (not shown) that extend into handle housing 210 and electrically couple controls 270 and motor 250 with the control unit to power motor 250 and control operation of tissue resecting instrument 10 in accordance with controls 270, the control unit, and/or other remote control devices, e.g., a footswitch (not shown). Cable 300 further includes one or more wires 310 that connect to an RFID transceiver 290 disposed within handle housing 210 towards the distal end thereof.

Drive rotor 260 is operably coupled with and extends distally from motor 250 such that, upon activation of motor 250, motor 250 drives rotation of drive rotor 260. Drive rotor 260 defines a base 262 and rotor body 264 extending distally from base 262. Base 262 is stationary and surrounds body 264. Rotor body 264 defines a non-circular cross-sectional configuration, e.g., a square or other polygonal configuration, and is configured for at least partial receipt within proximally-facing cavity 183e of proximal driver 182 of end effector assembly 100 in fixed rotational orientation relative thereto upon engagement of end effector assembly 100 with handpiece assembly 200 such that activation of motor 250 drives rotation of body 264 of drive rotor 260 to, in turn, drive rotation of proximal driver 182 of end effector assembly 100.

With reference to FIGS. 1 and 21-24, engagement of end effector assembly 100 with handpiece assembly 200 in preparation for use of tissue resecting instrument 10 is detailed. In order to engage end effector assembly 100 with handpiece assembly 200, end effector assembly 100 is approximated relative to handpiece assembly 200 such that lockout cap 170 and proximal extension 164 of hub housing 161 are inserted into internal bore 214 of handle housing 210 of handpiece assembly 200. As end effector assembly 100 is approximated in this manner, grasping ribs 169c of outer shell 168 of hub assembly 160 of end effector assembly 100 are grasped and squeezed inwardly towards one another, thereby causing the upper and lower surfaces of outer shell 168 to flex outwardly. As the lower surface of outer shell 168 is flexed outwardly, engagement finger 169a and engagement tooth 169b are likewise flexed outwardly. This enables end effector assembly 100 to be approximated further towards handpiece assembly 200 such that engagement tooth 169b is disposed in alignment with and below an engagement aperture 218 defined within handle housing 210 of handpiece assembly 200

Upon release of grasping ribs 169c of outer shell 168, the upper and lower surfaces as well as engagement finger 169a and engagement tooth 169b are returned inwardly towards their initial positions. In this manner, engagement tooth 169b is received within engagement aperture 218 to thereby engage end effector assembly 100 with handpiece assembly 200. Disengagement and release of end effector assembly 100 from handpiece assembly 200 is affected in the opposite manner.

As end effector assembly 100 is approximated relative to handpiece assembly 200 to affect the above-detailed engagement, body 264 of drive rotor 260 of handpiece assembly 200 is received within proximally-facing cavity 183e of proximal body portion 183a of proximal driver 182 in fixed rotational orientation therewith, e.g., due to the at least partially complementary configurations thereof, while base 262 of drive rotor 260 contacts a proximally-facing surface of proximal stop ring 172 of lockout cap 170 to urge proximal stop ring 172 distally against the bias of biasing member 176 (thereby compression biasing member 176). In this manner, tab 183d of proximal driver 182 is disposed relative to and removed from within recess 173 of proximal stop ring 172, thereby rotationally unlocking proximal driver 182 from lockout cap 170 and hub housing 161 and, thus, unlocking inner shaft 140 from fixed position relative to outer shaft 120 (see FIGS. 1-3).

With end effector assembly 100 engaged with handpiece assembly 200 as detailed above, RFID chip 190 of end effector assembly 100 is disposed in vertical registration with RFID transceiver 290 of handpiece assembly 200, e.g., wherein RFID transceiver 290 is radially aligned with and disposed radially-outwardly of RFID chip 190 relative to a longitudinal axis defined through end effector assembly 100 and handpiece assembly 200, due to the required orientation of end effector assembly 100 to enable engagement with handpiece assembly 200, e.g., such that engagement tooth 169b is received within engagement aperture 218. Thus, with end effector assembly 100 engaged with handpiece assembly 200, RFID transceiver 290 may read/write data to/from RFID chip 190 and/or communicate read/write data to/from the control unit, e.g., via cable 300.

The data stored on RFID chip 190 of end effector assembly 100 may include item number, e.g., SKU number; date of manufacture; manufacture location, e.g., location code; serial number; use count (which may be updated by writing data from RFID transceiver 290 to RFID chip 190); the home/initial position of inner blade 140; the rotation type (rotation versus oscillation); RPM settings (default, high, medium, low); max RPM; pressure setting information; vacuum setting information; outflow setting information; calibration information (e.g., amplification/attenuation information of gear assembly 186; and/or encryption key(s). Additional or alternative data is also contemplated.

Referring to FIGS. 1, 19, 20, and 23-24, with end effector assembly 100 engaged with handpiece assembly 200 as detailed above, tissue resecting instrument 10 is ready for use. In use, motor 250 of handpiece assembly 200 is activated to drive rotation of drive rotor 260. Upon activation of motor 250, with a head-start or delay relative to activation of motor 250, or independently thereof, suction is established through tissue resecting instrument 10, e.g., via activating the vacuum source of the fluid management system.

Activation of motor 250 drives rotation of drive rotor 260 which, in turn, drives rotation of proximal driver 182 to driver rotation of intermediate driver 188a to, in turn, drive rotation of distal driver 184. Rotation of intermediate driver 188a and distal driver 184 collectively rotates planetary gears 187b about the longitudinal axis of drive assembly 180 and within and relative to elongated ring gear 181 of hub housing 161. Rotation of planetary gears 187*b* within and relative to elongated ring gear 181 effects rotation of each planetary gear 187*b* about its axis due to its meshed engagement with elongated ring gear 181. The rotation of the planetary gears 187*b* about their axes, in turn, drives rotation of sun gear 187*a* due to the meshed engagement of planetary gears 187*b* with sun gear 187*a*. Sun gear 187*a*, in turn, drives rotation of inner shaft 140 relative to outer shaft 120 due to the fixed engagement of sun gear 187*a* about proximal end portion 142 of inner shaft 140.

The rotation of inner shaft 140 relative to outer shaft 120 and hub housing 161 also results in reciprocation of inner shaft 140 relative to outer shaft 120 due to the engagement of cam follower 163*c* within helical channel 185*e*. As inner shaft 140 is reciprocated relative to outer shaft 120, drive assembly 180 is similarly reciprocated relative to hub housing 161 and maintained operably coupled therewith as planetary gears 187*b* slide along and maintain meshed engagement within elongated ring gear 181. In this manner, the rotational input provided by motor 250 and rotor 260 results in reciprocation and rotation of inner shaft 140 relative to outer shaft 120, e.g., between the first, second, and third positions (see FIGS. 1-3).

Referring also to FIGS. 2 and 3, the reciprocation and rotation inner shaft 140 relative to outer shaft 120, together with the suction applied through inner shaft 140, enables tissue to be drawn through window 128 of outer shaft 120, cut by cutting edge 129 and/or cutting edge 149, and withdrawn proximally through inner shaft 140 via open distal end 146 thereof. The cut tissue, along with fluids and debris, are suctioned proximally through inner shaft 140 and out the open proximal end thereof, through intermediate driver 188*a* and out the open proximal end thereof, through proximal driver 182 exiting longitudinally-extending slot 183*h* thereof, through proximal extension portion 164 of hub housing 161 and exiting output opening 165 thereof, and ultimately through outflow path 220 of handpiece assembly 200 to outflow port 400 for output to the collection reservoir of the fluid management system.

Figure 19:
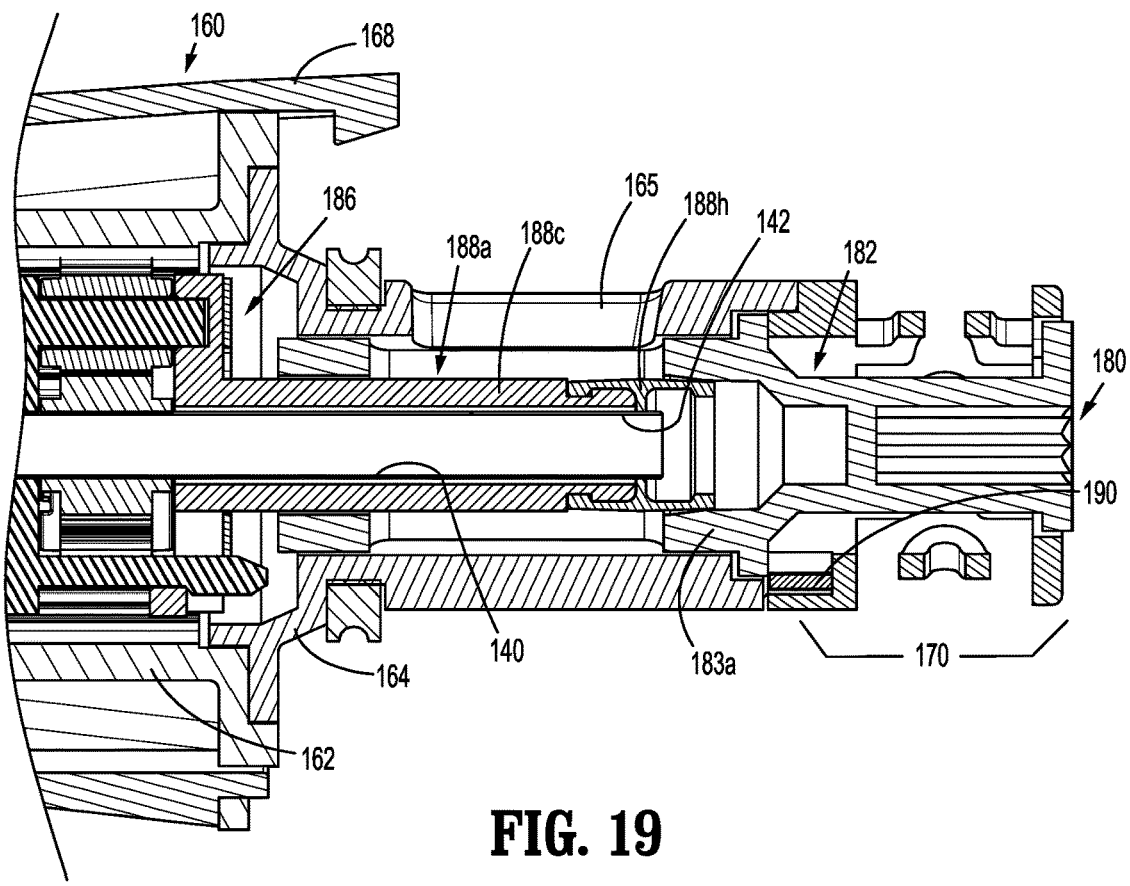
FIG. 19 is a side, longitudinal, cross-sectional view of a proximal end portion of the end effector assembly of FIG. 1 in the assembled condition, wherein the inner shaft is disposed in the first position.
Figure 20:
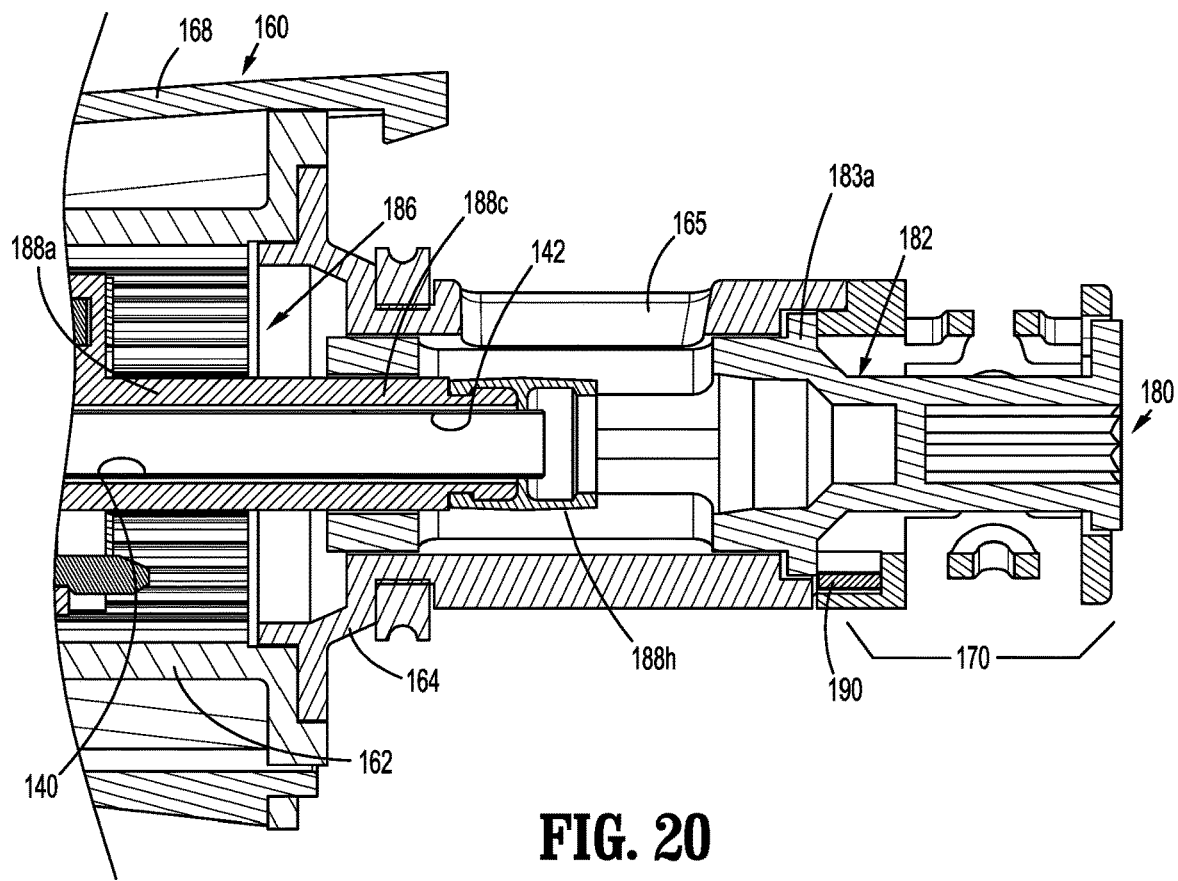
FIG. 20 is a side, longitudinal, cross-sectional view of the proximal end portion of the end effector assembly illustrated as in FIG. 19, wherein the inner shaft is disposed in the second position.
Figure 21:
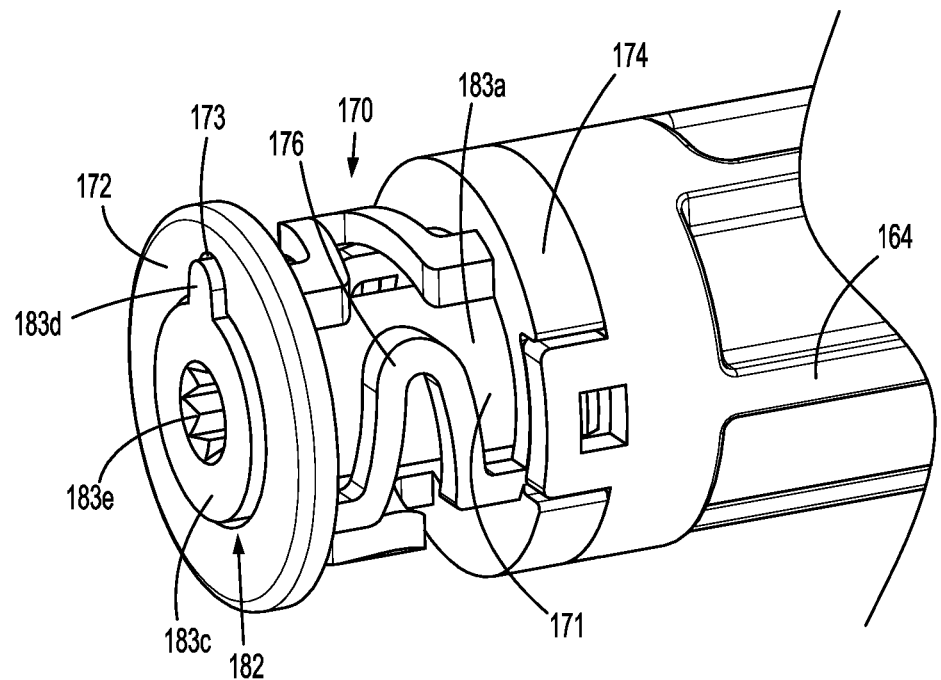
FIG. 21 is a side, perspective view of a proximal end portion of the end effector assembly of FIG. 1, wherein the lockout cap is disposed in an initial condition locking the inner shaft in position.
Figure 22:
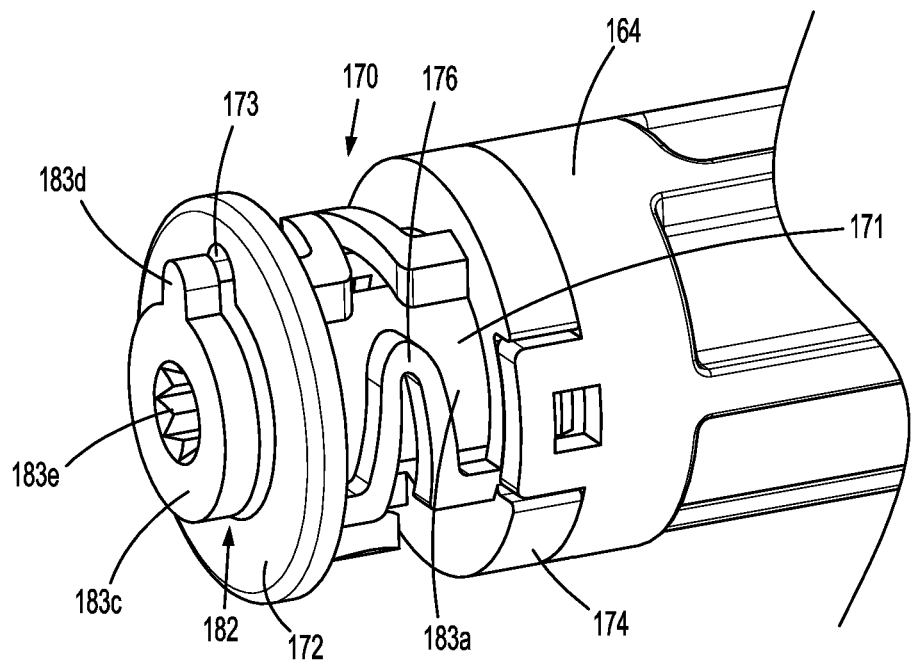
FIG. 22 is a side, perspective view of the proximal end portion of the end effector assembly as illustrated in FIG. 21, wherein the lockout cap is disposed in a compressed condition unlocking the inner shaft to permit movement thereof relative to the outer shaft.

With additional reference to FIGS. 19 and 20, as inner shaft 140 is reciprocated and rotated, seal 188*h*, engaged on the proximal end of intermediate driver 188*a*, is reciprocated (and, in embodiments, rotated at a different speed) through and relative to proximal driver 182. More specifically, seal 188*h* is reciprocated between a proximal-most position, e.g., the first position of inner shaft (FIG. 2), and a distal-most position, e.g., the closed position of inner shaft 140.

When seal 188*h* is disposed in or in close proximity to the proximal-most position, seal 188*h* establishes a fluid-tight seal against an interior surface of proximal driver 182 to thereby seals off the flow path of tissue, fluid, and debris out of the open proximal end of inner shaft 140. Thus, when seal 188*h* is disposed in or in close proximity to the proximal-most position, no suction is applied through inner shaft 140. When seal 188*h* is sufficiently displaced from the proximal-most position, the flow path is re-established, enabling tissue, fluid, and debris to be suctioned proximally through tissue resecting instruments 10 (FIG. 23), as detailed above.

Upon engagement of end effector assembly 100 with handpiece assembly 200, a control program (not shown) associated with motor 250 may record the rotational position of drive rotor 260 as a home position and, after activation, ensure that drive rotor 260 stops at a rotational position corresponding to the home position, e.g., the closed position of inner shaft 140 relative to outer shaft 120. The control program may utilize correlation information, e.g., from RFID chip 190, correlating, for example, rotation of drive rotor 260 with rotation of inner shaft 140 to ensure that inner shaft 140 is returned to the closed position relative to outer shaft 120 after each activation. Returning to the home position, corresponding to the closed position of inner shaft 140, also returns proximal driver 182 to its initial rotational position whereby tab 183*d* of external collar 183*c* thereof is rotationally aligned with recess 173 of proximal stop ring 172 of lockout cap 170 such that, upon disengagement and withdrawal of end effector assembly 100 from handpiece assembly 200, biasing member 176 returns proximal stop ring 172 proximally to thereby bias tab 183*d* into engagement within recess 173 and re-engage the lock fixing inner shaft 140 in the closed position relative to outer shaft 120.

Referring generally to FIGS. 1 and 23, as an alternative to handpiece assembly 200 configured for manual grasping and manipulation during use, tissue resecting instrument 10 may alternatively be configured for use with a robotic surgical system wherein handle housing 210 is configured to engage a robotic arm of the robotic surgical system. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely controls the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly of a tissue-resecting device, the end effector assembly comprising:
    an outer shaft including a hub housing disposed about a proximal end portion thereof;
    an inner shaft disposed within and rotatable relative to the outer shaft, the inner shaft including a sun gear disposed about a proximal end portion thereof; and
    a drive assembly rotatably disposed within the hub housing, the drive assembly including:
        a first driver rotatably disposed about the inner shaft distally of the sun gear;
        a second driver rotatably disposed about the inner shaft proximally of the sun gear;
        a plurality of planetary gears radially disposed about the sun gear in meshed engagement therewith, each planetary gear of the plurality of planetary gears rotatably mounted on a post extending between the first and second drivers; and
        a locking clip positioned proximally of the plurality of planetary gears and the sun gear, rotationally keyed to the second driver, and engaged with the first driver via at least one snap-fit engagement to thereby retain the first and second drivers and the plurality of planetary gears in operable engagement with one another and the sun gear such that a rotational input provided to the second driver drives rotation of the first driver, the plurality of planetary gears, and the sun gear to thereby drive rotation of the inner shaft.

2. The end effector assembly according to claim 1, wherein the hub housing including a ring gear disposed on an interior surface thereof, and wherein each of the planetary gears of the plurality of planetary gears is disposed in meshed engagement with the ring gear.

3. The end effector assembly according to claim 1, wherein the rotational input provided to the second driver drives rotation of the inner shaft at an output speed different from an input speed of the rotational input.

4. The end effector assembly according to claim 1, further including a third driver, wherein a portion of the third driver is slidably disposed about a portion of the second driver in fixed rotational orientation relative thereto such that rotation of the third driver provides the rotational input to the second driver.

5. The end effector assembly according to claim 1, wherein the first driver includes a helical channel defined therein and wherein the hub housing includes a cam follower engaged within the helical channel such that the rotational input provided to the second driver drives rotation and reciprocation of the inner shaft.

6. The end effector assembly according to claim 5, further including a third driver, wherein the third driver is slidably disposed about the second driver in fixed rotational orientation relative thereto such that rotation of the third driver provides the rotational input to the second driver, wherein the first and second drivers are configured to reciprocate relative to the third driver.

7. The end effector assembly according to claim 6, wherein the inner shaft includes a seal disposed about the proximal end thereof, the seal configured to selectively contact the third driver to seal off the proximal end of the inner shaft as the second driver is reciprocated within the third driver.

8. The end effector assembly according to claim 1, wherein the outer shaft defines a window towards a closed distal end thereof and the inner shaft defines an open distal end.

9. The end effector assembly according to claim 8, wherein at least one of the window of the outer shaft or the open distal end of the inner shaft is surrounded by a cutting edge.

10. The end effector assembly according to claim 1, further comprising a cap engaged with the hub housing, wherein engagement of the cap with the hub housing retains an RFID chip within a pocket defined within the cap.

* * * * *